(12) United States Patent
Lewallen

(10) Patent No.: US 6,895,973 B2
(45) Date of Patent: May 24, 2005

(54) PREVENTION OF DECUBITAL ULCERS USING IMPLANTED MAGNET

(75) Inventor: David G. Lewallen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 46 days.

(21) Appl. No.: 10/650,266

(22) Filed: Aug. 28, 2003

(65) Prior Publication Data
US 2004/0077922 A1 Apr. 22, 2004

Related U.S. Application Data
(60) Provisional application No. 60/406,468, filed on Aug. 28, 2002.

(51) Int. Cl.$^7$ ................................................ A61B 19/00
(52) U.S. Cl. ..................................................... 128/899
(58) Field of Search ................................. 128/897–899; 600/9–15; 297/284.3

(56) References Cited

U.S. PATENT DOCUMENTS

| | | | |
|---|---|---|---|
| 3,670,725 A | | 6/1972 | Gaylord, Jr. |
| 4,382,245 A | * | 5/1983 | Harrigan ..................... 335/306 |
| 5,054,142 A | | 10/1991 | Owens |
| 5,243,723 A | | 9/1993 | Cotner et al. |
| 5,473,313 A | | 12/1995 | Graebe, Jr. |
| 5,507,835 A | * | 4/1996 | Jore ............................. 623/36 |
| 5,529,568 A | * | 6/1996 | Rayman ........................ 600/9 |
| 5,876,364 A | | 3/1999 | Herbst |
| 6,349,439 B1 | | 2/2002 | Cook et al. |
| 6,367,106 B1 | * | 4/2002 | Gronsman ..................... 5/709 |
| 6,413,138 B1 | * | 7/2002 | Dokoupil ................... 446/129 |

* cited by examiner

Primary Examiner—Samuel G. Gilbert
(74) Attorney, Agent, or Firm—Quarles & Brady LLP

(57) ABSTRACT

A permanent magnet housed in a porous metal container is implanted in the pelvis of a subject and a second permanent magnet is attached to a supporting structure, such as the seat of a wheelchair. The opposing force produced by the two magnets when the subject rests on the supporting structure reduces the compressive force acting on the tissues therebetween.

4 Claims, 2 Drawing Sheets

PREVENTION OF DECUBITAL ULCERS USING IMPLANTED MAGNET

CROSS-REFERENCE TO RELATED APPLICATIONS

This application claims the benefit of U.S. Provisional patent application Ser. No. 60/406,468 filed on Aug. 28, 2002 and entitled "Prevention Of Decubital Ulcers Using Implanted Magnet".

BACKGROUND OF THE INVENTION

Pressure sores are a significant and common cause of morbidity and mortality in spinal cord injury (SCI) patients. Spinal cord injury (SCI) represents a significant health problem associated with life long disability and a broad range of secondary complications. Approximately 10,000 individuals incur a spinal cord injury in the United Sates each year. The costs of these injuries to both individuals and society are staggering. A recent cross-sectional multi-center study concluded that total direct costs for all cases of SCI are $7.736 billion in the United States (data provided in constant 1995 dollars) In addition, it has been estimated that the direct cost represents only 35% of the total aggregate costs of SCI to society. The remaining 65% are indirect costs associated with lost wages, fringe benefits, productivity, and leisure time.

Pressure related decubital ulcers present one of the most significant secondary complications of spinal cord injury, occurring in 10%–32% of SCI patients. The ischial tuberosity is the most common site for pressure sores, accounting for 28% of all ulcers. As much as 25% of the total cost of caring for spinal cord injury patients is spent on treatment of decubital ulcers. Considering the gradual decline in mortality rates from spinal cord injuries, coupled with an aging population, it is conceivable that the group of patients prone to developing pressure sores will increase in the future. The bulk of the literature to date has primarily focused on the technical aspects of surgical management of pressure sores.

The development of musculocutaneous flaps in the late 1970's revolutionized surgical management of pressure sores. Various musculocutaneous flaps have been used to treat ischial ulcers. However, long-term follow-up of those flaps has demonstrated wide variability in outcome and success rates. Reported recurrence rates of pressure sores repaired using musculocutaneous flaps range from 33%–80%. It is apparent that long-term therapeutic results remain sub-optimal and reliable alternatives in the management of pressure sores are highly desirable.

It is well established that the principle, and often solitary, cause of the decubital ulcers is excessive pressure, usually on a bony prominence in susceptible individuals. Sitting posture naturally creates high contact pressures at both ischial tuberosities, the coccyx, and in some cases the greater trochanters. The magnitude of contact pressure over ischial tuberosities has been found to correlate well with incidence of pressure sores. As a result of immobility and impaired protective sensation, wheelchair-bound SCI patients are at ongoing significant risk of pressure sores in these regions. Recently, various designs of wheel chair cushions have been introduced to relieve high contact pressure at the bony prominences. Ragan et al demonstrate that the highest seat-interface pressure is in the region located within 1 or 2 cm of the ischial tuberosity with maximum compressive stress inferior to the bottom surface of the ischial tuberosity. Some reduction of the pressure was obtained with an 8 cm thick cushion. However, increasing the cushion thickness beyond 8 cm was ineffective in further reducing subcutaneous stress.

Inflatable cushions currently available for wheelchairs have the inherent problems from air leaks, inaccurate adjustment, improper positioning, deterioration of the cushion, as well as over or under inflation. Changes in the inflation of these cushions occur due to leakage of the cushion or in the system, and with changes in temperature or altitude. These problems often result in the formation of sores and ulcers due to pressure points, especially in users with impaired sensation.

In addition, cushions are difficult to adjust, thereby decreasing the users mobility or necessitating assistance. The need for external pumps for inflation further complicates installment and use, and interferes with folding the wheelchair for travel or storage.

SUMMARY OF THE INVENTION

A new method for alleviating the pressure on a bony prominence using magnetic levitation has been developed. The method involves the implantation of a porous metal cylinder loaded with a permanent magnet into the ischial tuberosity to create a repulsive magnetic force between the magnet and a magnet embedded in the opposing support surface. This method alleviates excessive pressure on the bone prominence. This decrease of pressure allows for better perfusion of the soft tissues and prevents development of pressure related ulcers.

The present invention alleviates the pressure on bony prominences using magnetic levitation. The method involves implantation of hollow porous metal cylinders in the bone. Following osteointegration, the cylinder serves as an anchoring device for a permanent magnet which is disposed within the cylinder cavity. The opposing support surface contains an opposing magnet of like polarity oriented so that the magnetic field between the two magnets creates a controlled repulsive force. Because the magnet is implanted in bone, this repulsive, levitation force acts on the bone directly and spares the soft tissues the corresponding compressive force. This repulsive force can be made large enough to decrease pressure in the soft tissues overlying bony prominences sufficiently to allow for better perfusion of the soft tissues. This prevents the development of pressure related ulcerations.

DESCRIPTION OF THE PREFERRED EMBODIMENT

Figure 1:
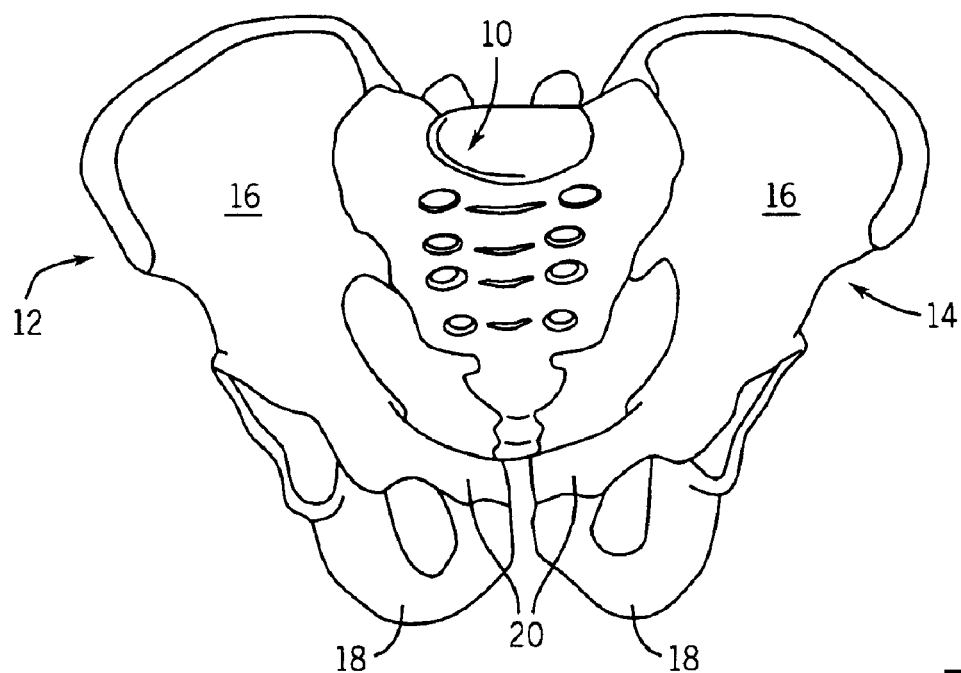
FIG. 1 is a perspective view of a human pelvis.
Figure 2:
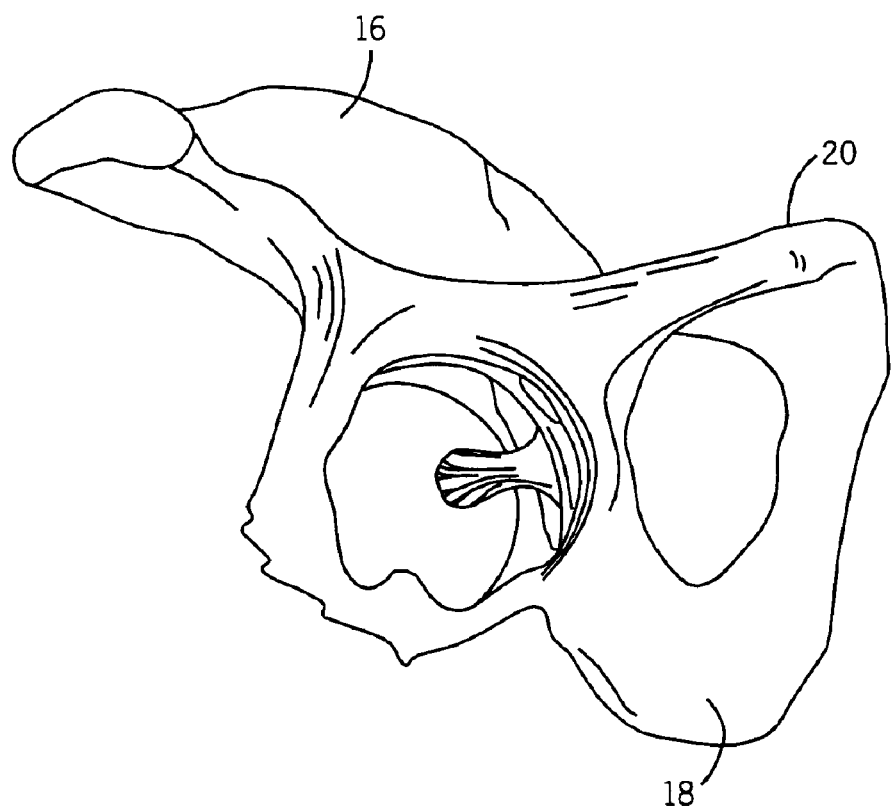
FIG. 2 is a partial perspective view of the pelvis of FIG. 1.

Referring particularly to FIGS. 1 and 2, the human pelvis is comprised of the sacrum 10 disposed between two coxal bones 12 and 14. Each coxa 12 and 14 makes up a lateral half of the pelvis and is comprised of a fused ilium 16, ischium 18 and pubis 20. When in the seated position, the ischium 18 is the lower-most point in the pelvis and it is at these two points that tissues are compressed the most due to the weight bearing down on a supporting structure such as a wheelchair seat.

Figure 3:
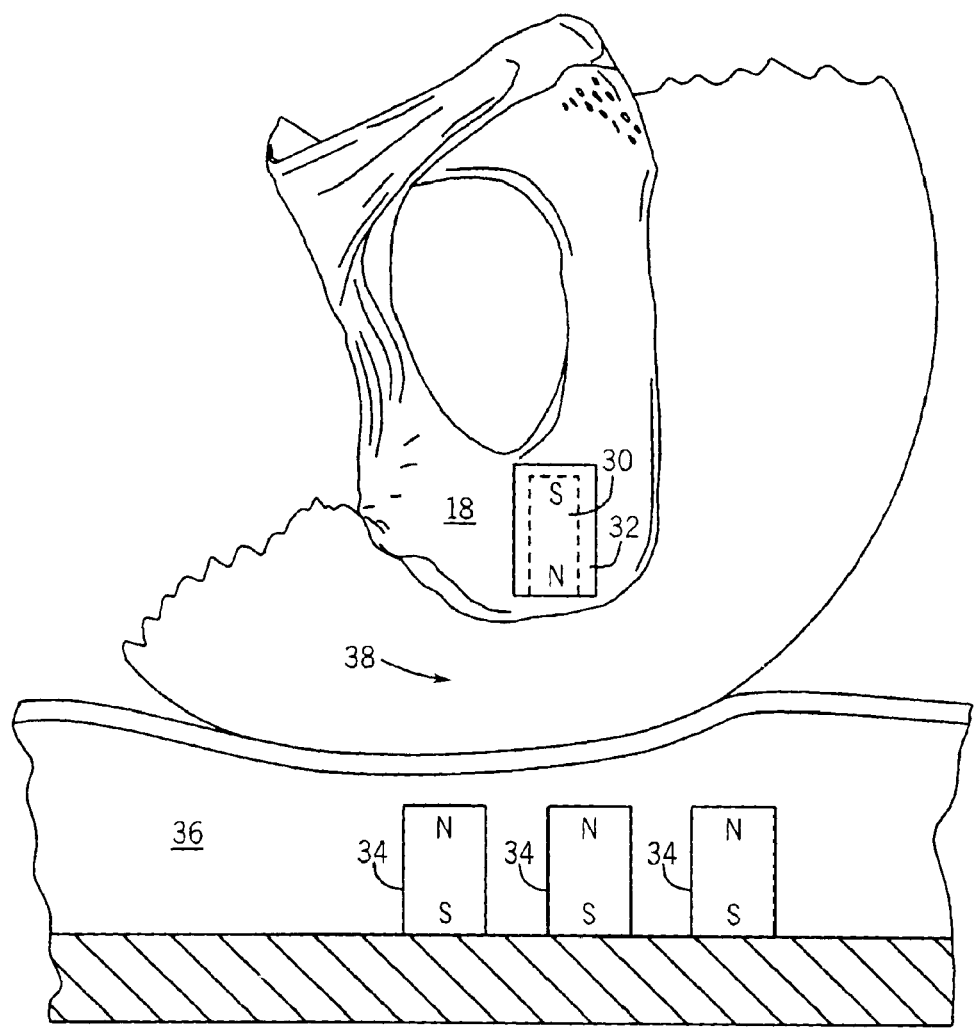
FIG. 3 is a side view with parts cut away of the pelvic region of a human subject seated on a chair showing permanent magnets implanted in accordance with a preferred embodiment of the invention.

Referring particularly to FIG. 3, the present invention is a method for reducing this compressive force on tissues in which a permanent magnet 30 is implanted in the ischial tuberosity 18. The circular cylindrical magnet 30 is housed in a circular cylindrical container 32 made of a porous metal. The porous metal is characterized by the fact that bone grows into the open pores in 6 to 12 weeks after implantation to securely lock the magnet 32 in its proper implanted location.

Opposing magnets 34 are mounted in the supporting seat cushion 36 to produce an opposing force that acts upward on the implanted magnet 30. Since the implanted magnet is embedded in the pelvic bone, this opposing force contributes to the support of the person on the cushion, but effectively bypasses the interceding soft tissues 38. The compressive force acting on the tissues 38 is thus reduced by the magnitude of the opposing force produced by magnets 30 and 34.

The ischial tuberosity bilaterally is exposed via a small incision near this bony prominence. Using Trephine system (Synthes, Pa., USA) a space 10×10 mm is created. To generate adequate repulsive force, a sufficient number of NeodyniumIronBoron permanent magnets (Magnetic Component Engineering, CA—dimensions: 10 mm in diameter and 5 mm height) are implanted into each ischial tuberosity 18. A single permanent magnet 30 generates a repulsive force of 500N. The magnetic field strength required to levitate the torso from the support surface depends on the torso's weight and is calculated as described below.

Equation 1 is used to obtain the force required to produce desired repulsive force over the bony prominence.

$$F = A \times P \quad \text{Eq. 1}$$

where F=repulsive force, A=area of application, and P=pressure.

The magnetic energy, W, stored in the soft tissue-filled gap between the magnet and support surface is given by Equation 2:

$$W = [h \times Z \times (B)^2]/2 \times \mu_0 \quad \text{Eq. 2}$$

where h=gap width between magnet and support surface; A=surface area of magnet; B=magnetic field flux density (Gauss,) and $\mu_0$=magnetic permeability of the material within the gap (skin or air=$1.26 \times 10^6$ Henrys/m$^2$).

The resulting repulsive force, F, is found by taking the first derivative of magnetic energy (given by Equation 2) with respect to the gap distance:

$$F = [d(W)]/dh = [A \times (B)^2]/(2 \times \mu_0) \quad \text{Eq. 3}$$

The magnetic field flux density, B, can be then solved for in terms of A, F, and $\mu_0$.

$$B = [(F \times 2 \times \mu_0)/A]^{1/2} \quad \text{Eq. 4}$$

The following assumptions were made with regards to these calculations:

1. Magnetic field strength is homogeneous throughout the surface of the magnet.
2. Magnetic permeability of skin and subcutaneous tissue is equal to that of air.
3. The magnet completely covers the underling support surface.

Preferably, the container is implanted in the bone without the magnet 30 and the bone is allowed to heal for 6 to 12 weeks. Then, an incision is made and the permanent magnet 30 having the prescribed strength is inserted into the porous container 32. While the magnet can also be implanted directly into the bone, an advantage of the container 32 is that it allows the bone to heal before any forces are applied which might cause the magnet to move or shift. Also, by using the container 32 the magnet 30 can more easily be removed and replaced with another magnet of different strength. This may be necessary, for example if the subject should undergo a significant weight change.

What is claimed is:

1. A method for reducing compressive force on soft tissues disposed between a bone and a supporting structure, the steps comprising;

implanting a permanent magnet in the bone; and imbedding a magnet in the supporting structure with its polarity aligned to create an opposing force with respect to the implanted magnet; and in which the bone is the ischial tuberosity of the pelvis of a human seated in a wheelchair and the supporting structure is the seat of the wheelchair.

2. A magnet assembly for reducing compressive forces on soft tissue disposed between a bone in a subject and a supporting structure, the combination comprising:

a first permanent magnet suitable for implantation into the bone; and a second permanent magnet fastened to the supporting structure and arranged such that a repelling force is produced that acts on the first and second magnets to reduce the compressive force acting on the soft tissues disposed therebetween; and in which the supporting structure is the seat of a wheelchair.

3. A method for reducing compressive forces on soft tissue disposed between the pelvis of a subject and supporting structure, the steps comprising:

implanting a first permanent magnet into a bone of the subject's pelvis; and fastening a second magnet to the supporting structure such that a repelling force is produced that acts on the first and second magnets to reduce the compressive force acting on the soft tissue disposed therebetween when the subject is seated on the supporting structure.

4. The method as recited in claim 3 which the first permanent magnet is implanted in the ischial tuberosity bone.

* * * * *